US011395927B2

United States Patent
Kim et al.

(10) Patent No.: US 11,395,927 B2
(45) Date of Patent: Jul. 26, 2022

(54) HEAD NECK IMMOBILIZATION WRAP (71) Applicant: Thomas Jefferson University, Philadelphia, PA (US)

(72) Inventors: Hyun Kim, Drexel Hill, PA (US); Voichita Bar Ad, Wynnewood, PA (US); Amy Taylor, Quakertown, PA (US); Shivank Garg, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 473 days.

(21) Appl. No.: 16/478,172

(22) PCT Filed: Jan. 22, 2018

(86) PCT No.: PCT/US2018/014674
§ 371 (c)(1),
(2) Date: Jul. 16, 2019

(87) PCT Pub. No.: WO2018/136868
PCT Pub. Date: Jul. 26, 2018

(65) Prior Publication Data
US 2019/0351255 A1  Nov. 21, 2019

Related U.S. Application Data

(60) Provisional application No. 62/448,467, filed on Jan. 20, 2017.

(51) Int. Cl.
*A61N 5/10* (2006.01)
*A61F 5/37* (2006.01)

(52) U.S. Cl.
CPC .......... *A61N 5/1049* (2013.01); *A61F 5/3707* (2013.01); *A61F 5/3776* (2013.01); *A61N 2005/105* (2013.01); *A61N 2005/1097* (2013.01)

(58) Field of Classification Search
CPC ........ A61F 5/37; A61F 5/3707; A61F 5/3769; A61F 5/3776; A61F 2009/0035;
(Continued)

(56) References Cited

U.S. PATENT DOCUMENTS 5,081,665 A * 1/1992 Kostich ................ A61B 6/0421
128/845
5,337,760 A  8/1994 Nichols
(Continued)

FOREIGN PATENT DOCUMENTS

| CN | 106580535 A | * | 4/2017 |
| WO | 2011139924 A2 | | 11/2011 |
| WO | 2016108154 A1 | | 7/2016 |

OTHER PUBLICATIONS

Amelio, D., et al., "Analysis of inter-and intrafraction accuracy of a commercial thermoplastic mask system used for image-guided particle radiation therapy", Journal of Radiation Research, vol. 54, Suppl. 1, pp. i69-i76, 2013.
(Continued)

*Primary Examiner* — Thaddeus B Cox
*Assistant Examiner* — Marc D. Honrath
(74) *Attorney, Agent, or Firm* — Cozen O'Connor (57) ABSTRACT

An immobilization apparatus having at least one or more straps that engage a surface; wherein at least one of the straps comprises a force gauge to determine the amount of force applied to a patient immobilized with said straps; wherein the position of the patient is replicable for treatment of radiation and other head or neck treatments.

18 Claims, 9 Drawing Sheets

(58) Field of Classification Search
CPC ...... A61N 5/10; A61N 5/1048; A61N 5/1049;
A61N 2005/105; A61N 2005/1092; A61N
2005/1097; A61B 8/40; A61B 8/4227;
A61B 6/04; A61B 6/0407; A61B 6/0414;
A61B 6/0421; A61B 90/14
See application file for complete search history.

(56) References Cited

U.S. PATENT DOCUMENTS

| | | | |
|---|---|---|---|
| 5,342,290 | A | 8/1994 | Schuellein |
| 5,797,924 | A | 8/1998 | Schulte et al. |
| 6,143,003 | A | 11/2000 | Cosman |
| 6,244,270 | B1 | 6/2001 | Lutian et al. |
| 6,435,188 | B2 * | 8/2002 | Tyrrell .................. A61F 5/055 128/870 |
| 6,637,057 | B2 | 10/2003 | Phillips et al. |
| 6,945,251 | B2 | 9/2005 | Woodburn, III |
| 7,802,576 | B2 | 9/2010 | Cuypers et al. |
| 8,093,564 | B2 | 1/2012 | Balakin |
| 8,567,405 | B2 | 10/2013 | Arn et al. |
| 2002/0016600 | A1 | 2/2002 | Cosman |
| 2007/0101501 | A1 | 5/2007 | Tomcany et al. |
| 2008/0269030 | A1 * | 10/2008 | Hoffman ............... A61H 1/0218 482/142 |
| 2010/0091948 | A1 | 4/2010 | Balakin |
| 2011/0240042 | A1 * | 10/2011 | Cooke .................... A61G 5/12 128/870 |
| 2011/0295317 | A1 * | 12/2011 | Busch, III ................ A61F 5/04 606/241 |
| 2012/0158055 | A1 * | 6/2012 | Graham ............. A63B 21/4034 606/237 |
| 2012/0199131 | A1 * | 8/2012 | Sofranko ............. A61M 16/06 128/206.21 |
| 2016/0296401 | A1 * | 10/2016 | Cole .................... A61G 13/101 |
| 2017/0303859 | A1 * | 10/2017 | Robertson ............. A61B 5/721 |

OTHER PUBLICATIONS

Duma, M.N., et al., "A novel setup approach for helical tomotherapy in head and neck cancer: A case report", Oncology Letters, vol. 6, pp. 1470-1474, 2013.

International Search Report issued in International Application No. PCT/US2018/014674 dated Mar. 29, 2018.

Li, G., et al., "Migration from full-head mask to "open-face" mask for immobilization of patients with head and neck cancer", Journal of Applied Clinical Medical Physics, vol. 14, No. 5, pp. 243-254, 2013.

* cited by examiner

HEAD NECK IMMOBILIZATION WRAP

CROSS REFERENCE TO RELATED APPLICATIONS

This is a United States National Stage application of International Patent Application No. PCT/US2018/014674, filed Jan. 22, 2018, published as WO 2018/136868 on Jul. 26, 2018, which claims priority to U.S. Provisional Patent Application No. 62/448,467, filed Jan. 20, 2017, the entirety of each of which is incorporated herein by reference.

FIELD OF INVENTION

The present application is generally related to immobilization devices, in particular for immobilization of the head and neck during a medical diagnostic or treatment procedure, and more particularly to an apparatus which permits precise and reproducible positioning of a patient's head and neck during radiation therapy, without the need for a frame or mask like feature.

BACKGROUND OF THE INVENTION

Numerous medical diagnostic and treatment procedures require that a patient's skull, head, and/or neck is immobilized during the treatment. Furthermore, in many cases, for subsequent treatments, it is also necessary to reproduce the exact position of the patient's skull, head, and/or neck for further treatment. One such example is radiation therapy, which is used to deliver targeted doses of radiation to a target, such as a tumor. Several techniques and devices have been developed to aid in immobilizing the patient's head to deliver radiation. See, for example, U.S. Pat. Nos. 5,797, 924, and 6,945,251. Additional patents identify other mechanisms and devices to secure the head or the body for treatment or for immobilization of the individual. For example, see U.S. Pat. Nos. 5,337,760, 6,143,003, 6,244, 270, 6,435,188, 6,637,057, 8,093,564, 8,567,405.

Immobilization of the patient during treatment is of paramount importance to ensure that the radiation is delivered to the specific location to treat the specific target, and diminish radiation to otherwise healthy cells. A common immobilization device for radiation therapy is a thermoplastic mask, which covers the face, head, and neck of the patient, and holds the head in a reproducible location, wherein the radiation therapy can be performed over several different patient sessions and accurately administer the radiation to the precise same location on each therapeutic session.

However, for many patients, the thought of being immobilized and held into place by a mask is simply terrifying. For example, those that suffer from various degrees of claustrophobia are simply unable to utilize these masks. Even those that typically are not claustrophobic also find such masks to be uncomfortable and thus patients may shy away from successful radiation therapy treatments to avoid the use of such devices. Further, current mask technology does not allow for control of the degree of extension of the head. Weight loss and tumor shrinkage can also make the mask too loose for reliable patient positioning, thereby reducing the reliability of the masks in some situations. When a mask is too loose the patient must undergo radiation planning again, adding to cost, patient inconvenience, and physician time.

Additional literature, for example, J. Appl. Clin. Med. Phys, 2013, Sep. 6: 14(5); 243-54, doi 11.1120/jacmp.v14i5.4400 entitled "Migration from full-head mask to "open-face" mask for immobilization of patients with head and neck cancer, Li g. et al.; J. Radiat. Res. 2013 July; 54 Suppl 1: i69-76. Doi 10.1093/jrr/rrt038 entitled "Analysis of inter- and intrafraction accuracy of a commercial thermoplastic mask system used for image-guided particle radiation therapy; Amelio et. al; and Oncology Letters, Monday Sep. 2, 2013; vol. 5 no 5: 1470-1474. Doi: 10.3892/ol2013.1558 M. Duma, et. al, each address certain limitations with regard to full face mask systems. Indeed, despite their clinical use, such masks remain problematic for many patients, due to their restrictive nature.

However, no system has currently devised a reproducible immobilization device that eliminates the need for a thermoplastic mask, or other specialized restricting device, many of which need to be custom fit to the patient, for radiation or other medical treatments where replication of a position is required. Further, no invention allows for control of the degree of a patient's neck extension to improve patient setup and reliability.

SUMMARY OF THE INVENTION

In accordance with these and other objects, a first embodiment of a head and neck immobilization device, is directed to an apparatus that provides for a first strap extending over the forehead of a patient and second strap extending over the chin of a patient, wherein each strap is connected on at least one side to a force engaging member, such that replicable force can be applied to each strap so as to position the patient in a replicable position for treatment.

According to another embodiment, an apparatus that provides for a first strap extending over the forehead of a patient and second strap extending over the chin of a patient, wherein the patient is positioned on a head/neck cup; and wherein each strap is connected on at least one side to a force engaging member which is secured along an edge of a table surface, such that replicable force can be applied to each strap so as to position the patient in a replicable position for treatment.

According to another embodiment, a method of immobilizing a patient comprising the steps of: engaging a first strap over the forehead of a patient, engaging a second strap over the chin of said patient; determining the force applied to each strap; applying radiation therapy to the patient; and wherein said position determined by said first and second straps can be replicated by determining the force, length and angle relative to treatment table of each strap so as to replicate the position of the patient for subsequent therapy.

A further embodiment is directed to an apparatus having two straps, positioned so as to extend from the head and around the chin, and the second positioned near the chin and which extends around the forehead, wherein each strap is connected to a force gauge, so as to quantify and determine the force and length of the strap.

A further embodiment is directed to an immobilization device for replicable positioning comprising a surface having two sides, a face surface, and a top; a first and a second strap, at least one force gauge, at least one clamp, and at least one nose bridge; said first strap positioned across said face surface and having connection means to connect to each of the two sides of the surface; said second strap positioned at a different point than said first strap, but also positioned across said face surface, and having connection means to connect to each of the two sides of the surface at a different point that said first strap, wherein at least one of the first or second strap comprises the at least one force gauge connected to one end of the first or second strap; said at least one clamp being positioned adjacent to said force gauge and capable of securing said first or second strap; and said nose bridge positioned between said first and second strap above said surface.

A further embodiment is directed towards a replicable immobilization device comprising: A surface, two strap, and a force gauge; wherein the surface is substantially flat having a surface face, a length and width sufficient to support a human patient, a top and, two sides; the first strap is attached on one end to one side of the surface, the opposing end being free; wherein the free end, crosses over the surface face and engages a connecting means on the opposing side of the surface; the second strap having one end secured on one side of the surface and the opposing end of the second strap being free; said free end of the second strap engaging to a connecting means on the opposing side, and engaging with a force gauge on the opposing side; wherein the force gauge quantifies a force applied to the strap; wherein the quantified force can be replicated for subsequent immobilization.

In a preferred embodiment, the device comprises a second force gauge.

In certain embodiment, the free end of each strap comprises an attachment means to secure to a force gauge. In yet other embodiments, the connecting means is defined as a first and second strap anchor positioned on one side of the surface for connecting the free end of the first and second straps. In further embodiments, the first and second strap anchors comprise a clamp for securing a strap to the strap anchor. In yet another embodiment, the straps comprise a D-ring at the opposing end of the strap, wherein the D-ring engages to a force gauge.

In a preferred embodiment, the immobilization device further comprises a nose bridge and a laser, said nose bridge comprising a marker for engaging to said laser for orienting the nose bridge to a specific location based on the laser position.

A further embodiment is directed towards a method of immobilizing a patient for radiation therapy comprising: securing a first strap to a radiation therapy table, one end of said strap engaged to one side of the radiation therapy table, and the opposing end crossing over said radiation therapy table and securing to a strap anchor on the opposing side of the radiation therapy table; securing a second strap to said radiation therapy table, one end of said second strap connected to one side of the radiation therapy table and the opposing end of the second strap connected to a force gauge; wherein said second strap engages with said patient to define a degree of neck extension; and administering radiation therapy to said patient.

In certain embodiments, a further step comprise securing a third strap to said ration therapy table.

In certain embodiments, a further step in the above method is comprises placing a nose bridge between the first and second straps, wherein said nose bridge is engaged to said patient. In certain embodiments, said nose bridge comprises a marker, wherein a further step comprises detecting said marker with a laser.

In certain embodiments, a further step comprises determining a force from the force gauge and determining a degree of neck extension; wherein said force and neck extension can be replicated for re-positioning of the patient for a subsequent round of radiation therapy.

A replicable immobilization device comprising: a surface, a first and second strap, and two force gauges; wherein the surface is substantially flat and has a length and width sufficient to support a human patient, a top edge and two side edges; the first strap having a first end connected to one side edge, and the opposing end connected to the opposing side edge, wherein a portion of the strap contacts the a portion of the body being immobilized; the second strap having a first end connected to one side edge, and disposed between the first strap and the top edge, and the opposing end connected to the opposing side edge, also between the top edge and the first strap, wherein a portion of the strap comprises a concave recess for securing around a portion of the body being immobilized; each of the first and second straps comprises a force gauge positioned on the first and second strap, wherein the force gauges provide a reading of the force applied to each strap.

In a further embodiment, the device further comprises a neck cradle positioned on the surface.

In a further embodiment, the device further comprising a nose bridge, said nose bridge formed from a thermoplastic material, said nose bridge comprising a marker disposed of on a top surface of said nose bridge. In certain embodiments, said marker comprises a pair of intersecting lines; and wherein said device further comprises at least one laser, said laser oriented to intersect with at least one of the intersecting lines of said nose bridge to define a position of said nose bridge.

In certain embodiments, the straps are defined at a predetermined angle, wherein each strap defines a strap orientation angle, as compared to flat surface of table, wherein the strap orientation angle and the force define a specific immobilization parameter.

In certain embodiments, the force gauge is parallel to the direction of the strap.

In certain embodiments, the immobilization device wherein a first and second strap anchor are positioned on the opposing side of the surface, and a clamp positioned on each first and second strap anchor. In preferred embodiments, wherein said clamp receives an opposing end of a strap and wherein said clamp operates between an open and a closed position, suitable to secure a strap to said strap anchor.

In a preferred embodiment, use of the immobilization device as described herein to immobilize a human patient for radiation therapy.

Additional features and embodiments will be apparent to one of ordinary skill in the art upon consideration of the following detailed description of preferred embodiments and descriptions of the best mode of carrying out the invention.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

The words "table" and "surface" are used interchangeably to refer to the apparatus on which the patient is positioned. A table or surface may be a flat table, or a chair or couch or other surface suitable for positioning the patient and performing the treatment.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The present invention is related to an apparatus and methods for using said apparatus for securing the head of a patient for treatment. In particular, in preferred embodiments, the apparatus is utilized to secure the head of the patient for radiation therapy.

Traditional therapeutic masks and immobilization devices use thermoplastic masks that surround the face of the patient and create significant issues for patients having any type of claustrophobia. Furthermore, such devices are expensive, cumbersome, and are not suited for use with all patients. Indeed, the requirement to store such a device is, in itself, a problem that has yet to be solved, as the masks are fragile and cumbersome.

The immobilization device as described in the embodiments herein utilizes a series of straps that are attached to a surface, wherein the straps are tightened to impart a precise force upon a patient, when the patient is laying on the surface. These precise forces from the straps, enables the patient to be reproducibly immobilized on the surface to ensure that several courses of radiation therapy are performed on the same precise location during each radiation therapy session, which may occur over several days, weeks, or months. However, the device, by use of several straps, eliminates the use of and need for claustrophobic facial masks that are otherwise common for such immobilization.

Figure 1:
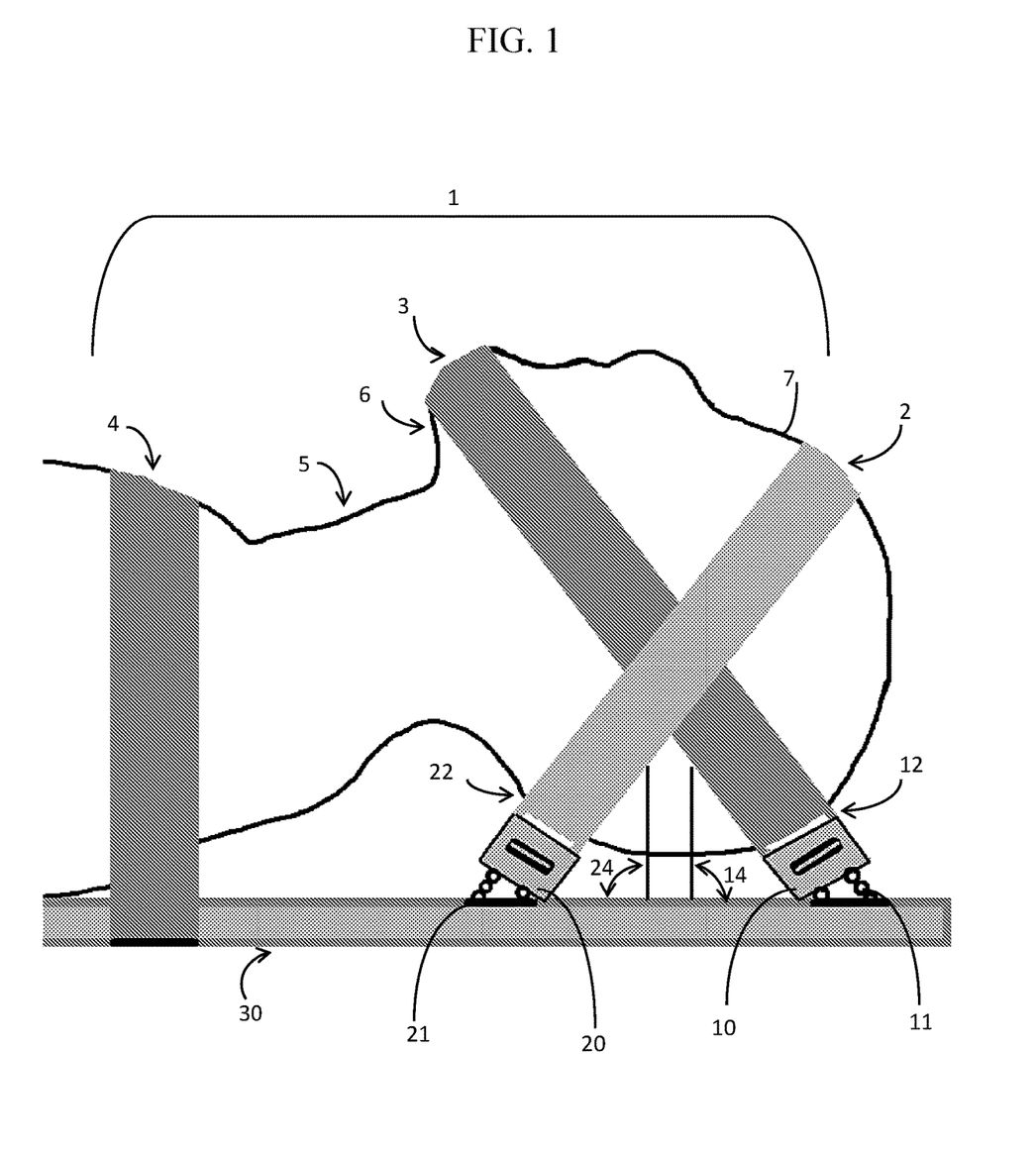
FIG. 1 provides a depiction of an immobilization device described herein.

In view of FIG. 1, a patient 1 is depicted laying down on a surface 30, and having three straps 2, 3, and 4 in contact with the patient. Shoulder strap 4 is attached below the neck 5, and secures over the body of the patient at or about the shoulder level. The shoulder strap 4 is intended to keep the patient's torso and shoulder region stable on the surface 30. The shoulder strap 4 is secured to or around the surface 30 on each side of the patient 1.

Moving from the patient's chest to the head, the next strap to contact the patient is the chin strap 3 which contacts the patient 1 at or around the chin 6. The chin strap 3, while contacting the patient at the chin 6, is connected to the surface 30 at or around the top of the head 12. This provides an angle 14 between the chin strap 3 and the surface 30. The chin strap 3 is secured on each side of the patient to the surface 30, and located on one side of the strap is a force gauge 10. The force gauge 10 is secured to the surface 30 with a connection means 11, depicted here as a chain 11. Any means known in the art to connect the force gauge 10 to the surface 30 can be utilized, including adhesives, threaded fasteners, snaps, string, wire, chain, ropes, bolts, or other mechanisms as known to one of ordinary skill in the art.

In certain embodiments, the angle 14 is moved to be perpendicular to the board. This assists with confirming consistent readings on the strain gauges to ensure reproducibility of the position of the patient. It is preferable to use a chin strap on the chin. For example, the straps utilized with various helmets have a concave portion to the strap that slightly cups the chin and assists in both comfort and fit of the strap at this position.

Moving from the chin towards to the forehead, the third strap is the forehead strap 2, which attaches to the surface 30 near the base of the head 22 and contacts around the forehead 7. An angle 24 provides the angle of orientation between the attachment points on the surface 30 to the forehead 7. A force gauge 20 is utilized to secure the forehead strap 2 to the surface 30 via an attachment means 21 that is similar or identical to the attachment means for the chin strap 3. The strap over the forehead may include a soft or compressible pad to be placed over the forehead for comfort.

The force gauge 10 provides a mechanism that allows a user to both determine a particular force to be applied, and to apply that force through the strap. Accordingly, when a patient is positioned on the surface 30, the chin strap 3 may be determined to have a force of X and the forehead strap a force of Y. The forces are determined only by initially placing the patient on the surface 30 and attaching the straps 2, 3, and 4, to the patient and stabilizing the head and neck for treatment. The force gauges allow calibrating the straps to provide immobilization and neck extension position without compromising patient comfort and safety. Strap immobilization without force gauges may result in poor immobilization or the risk of pressure ulcers from repeated excess pressure to skin. Once the patient is properly positioned, the force gauges 10 and 20 are read and the appropriate force is determined for at least the straps 2 and 3. There is a plastic head and neck holder (cup)/cradle 40 under the patient's head which is the standard for supporting the patient's head during immobilization. In certain embodiments, it is important to have the force gauge parallel to the direction of the strap. This assists in accurately quantifying the amount of force on the strap to ensure reproducibility.

In certain embodiments, the straps 2 and 3 may be aligned perpendicular to the support, and thus strap 2 can be the chin strap and strap 3 can be the forehead strap. This prevents the straps from crossing.

Upon completion of a treatment, the straps 2, 3, and 4 are released and the patient is free to go. In providing treatment to a patient, reproducibility of the position of the patient and position of the radiation treatment is paramount to consistent and effective treatment of the patient. Accordingly, the thermoplastic masks are effective in particularly immobilizing the patient and providing highly reproducible positioning of the patient for repeated treatment. However, by reading the force for each of the gauges, and reapplying that same force to the gauges, the patient's position, and particularly the position of the head and neck, can be reproduced to allow for targeted treatment with radiation therapy.

It is particularly suited that forces for the forehead strap 2 and the chin strap 3 are determined when the patient is in a comfortable resting positon on the surface 30, so that the patient can be repeatedly placed into this positon and be immobilized for a duration of time sufficient for treatment.

Figure 9:
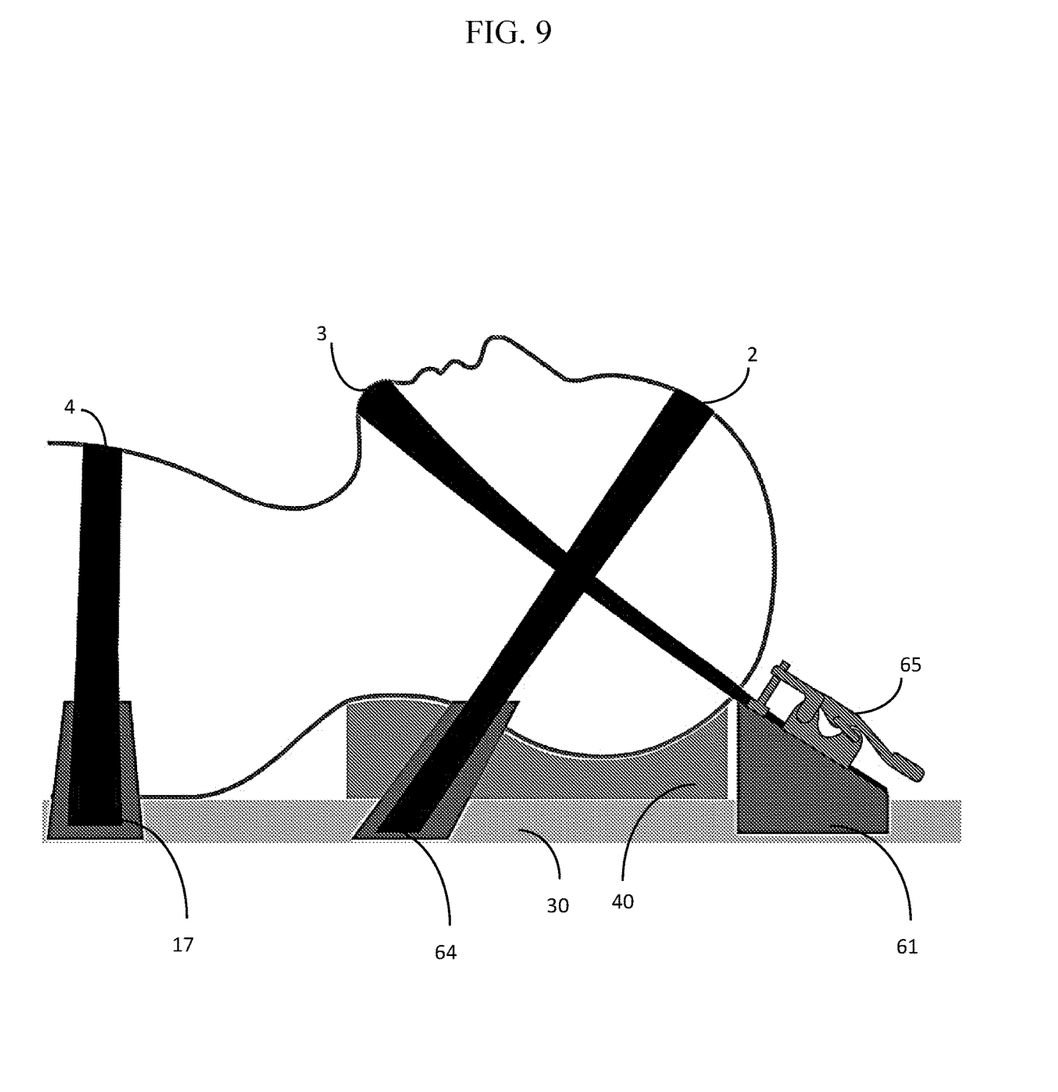
FIG. 9 depicts an example of a three strap system, using a clamp.

FIG. 9 further details a similar setup to FIG. 1, but also utilizes a clamp 65, and three connection means, which are anchors 17, 64, and 61. These anchors secure to the sides of the table, and provide a stable mechanism to latch each of the straps. For example, the clamp 65 can be used to secure the strap, though other securing means are suitable, especially to strap 4, which does not need a precise force application.

Figure 2:
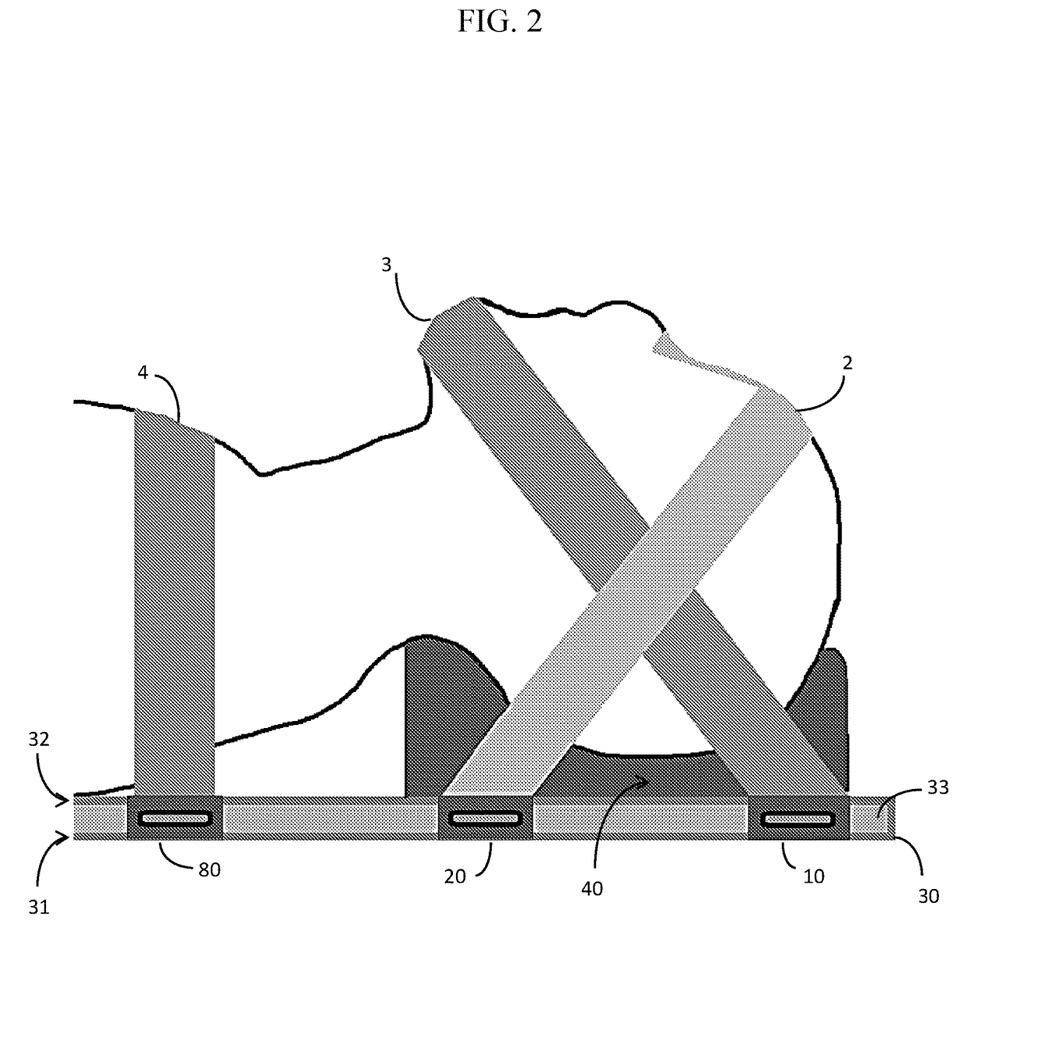
FIG. 2 provides a depiction of additional features of an embodiment of the immobilization device.

In further embodiments, e.g. as depicted in FIG. 2, the force gauge can be integrated into the table itself. In other words, the surface of the force gauge may be flush with that of the treatment table 30. The force gauges may be connected to the table 30 at varying positions. If the gauges are integrated into the table, each gauge can be selectively moved along the axis of the table to different positions to allow for different angles of immobilization. The force gauge position is thus set according to predetermined positions on the table and at specified distances from the patient.

In certain embodiments, additional features may be utilized to aid in positioning the patient for reproducible immobilization. FIG. 2 provides a head/neck cradle 40 that aids in positioning the patient in the proper location for reproducibility of the patient. Accordingly, the patient is placed on the surface 30 and places their head on the head/neck cradle 40. Then the shoulder strap 4 is attached, the chin strap 3 and the forehead strap 2 are secured. Appropriate pressure is applied and measured on the force gauges 20, 10, and 80 to place the patient in the appropriate position. To reproduce the position, the precise force is applied to at least the two force gauges 10 and 20 to ensure consistent patient position. In preferred embodiments the force gauge 80 is also utilized to assist in patient positioning.

The force gauges 10, 20, and 80, as depicted in FIG. 2 are attached to the side of the table 30. These force gauges 10, 20, and 80 can be embedded in the side of the table. However, in preferred embodiments, the force gauges 10, 20, and 80 engage to a track like system on the side of the table 30, having an upper track 32 a middle track 33 and a lower track 31. The force gauges 10, 20, and 80 engage with one, two, or all three of these track components. Accordingly, the track provides a mechanism to allow for the gauges to be selectively moved along the side of the table 30 and to be locked and secured in place for a treatment, but moved thereafter for a subsequent treatment needing the gauges in different locations.

A further embodiment includes the feature where the straps, 2, 3, and 4 have a mechanism to determine the proper length of each strap. Accordingly, the strap has a mechanism to set and modify the length of the strap. Accordingly, for each patient, a strap length is quantified and a strap force is determined for the force gauge 20 and 10. Utilizing the same strap length and the same strap force allows reproducibility of the location of the patient for subsequent immobilization for treatment.

A further embodiment comprises a ratchet type mechanism that can modify the force/tension along the strap. For example, the attachment means 21 and 11 can include such mechanism to lengthen or shorten these attachment means. This provides a different mechanism to determine the proper length of the strap for the particular patient.

Figure 3:
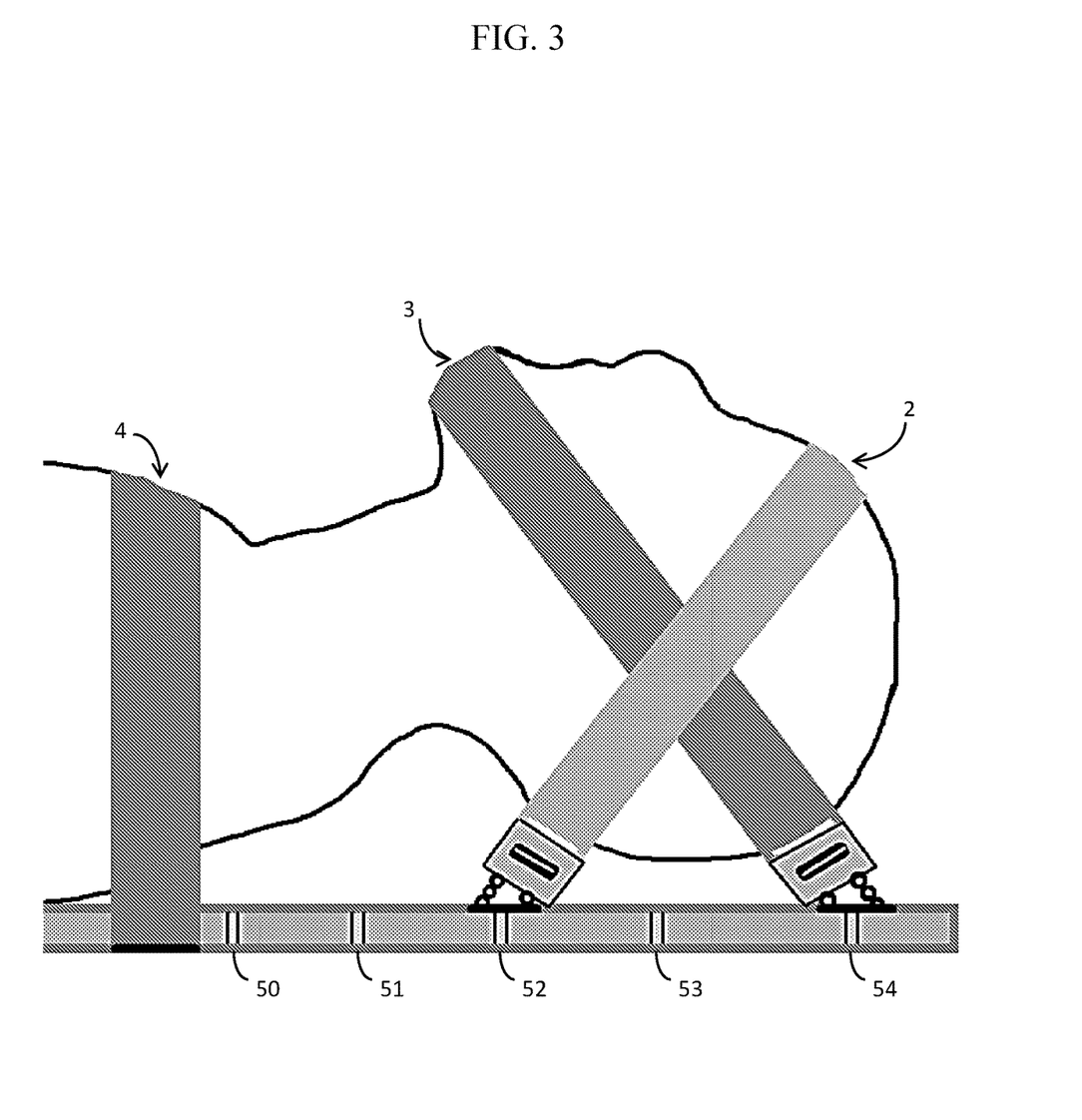
FIG. 3 provides a further depiction of an embodiment of the immobilization device.

Finally, a ratchet type mechanism that simply pulls onto the strap can be utilized. This ratchet type mechanism may be incorporated into and with the force gauges 10 and 20. Using a pre-determined length of strap, the ratchet can quantify the exact length of the strap and the appropriate pressure applied by that strap to replicate the position of the head.

Where the strap length is proper, but the pressure is incorrect, the patient's head or neck can be adjusted to ensure proper placement. Indeed, FIG. 3 provides placement notches 50, 51, 52, 53, and 54 that correspond to positions on the surface to aid in placement of the patient. For example, position 50 aligns with the top of the shoulder. Position 51 aligns with the bottom of the neck. Position 52 aligns with the base of the head and the point for the top of the chin strap 3. Position 53 aligns with the bottom of the ear and center point for the straps to cross. And position 54 aligns with the top of the forehead and the top of the forehead strap 2. In further embodiments, placement notches may include additional notches to define additional locations. These notches are attached to the support 30 and such notches are able to be moved for each patient. For example, the notches may simply be a measuring tape or notches from the top of the support 30. These positions can then be noted in the patient's file and aid in initial placement of the patient and of the straps as the straps are being adjusted for correct positioning in subsequent uses. These notches, therefore, provide an additional feature to aid in the reproducibility of the position of the patient. These notches are positioned on each side of the surface, and in preferred embodiments, the left and the right are mirror images of one another, to allow for consistent positioning and immobilization of the patient.

Furthermore, these notches can be utilized with the sliding gauges to aid in moving the gauges and securing them into a precise location. Indeed, the notches can further assist by providing additional locking mechanisms that engage to the gauges and allow for selectively secure positioning of the gauges. Other suitable sliding mechanism do not require notches to secure the gauge, and such mechanisms are known to one of ordinary skill in the art. Accordingly, a simple measuring system to mark positions can be utilized with the invention. Alternatively, electronic or mechanical systems can be used to accurately place the gauges along a defined point on the table.

Figure 4:
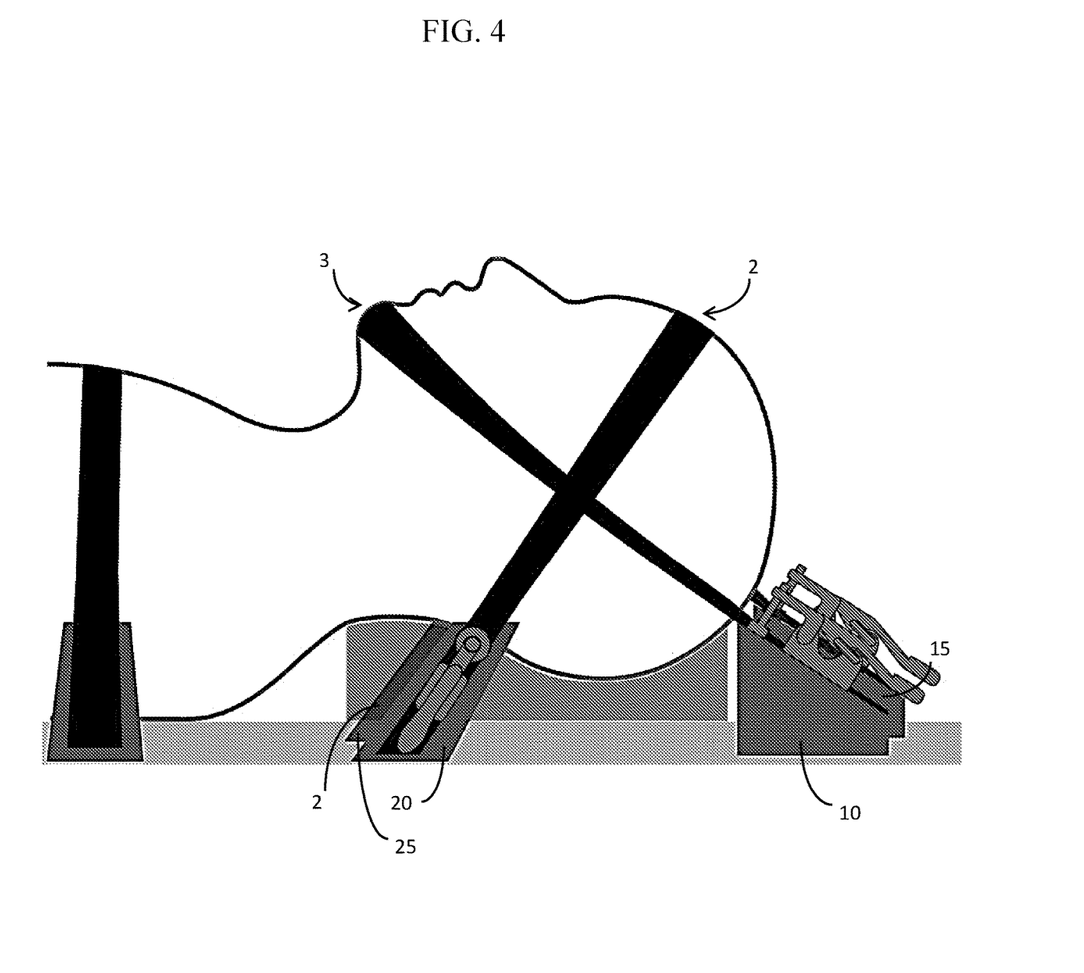
FIG. 4 provides a further depiction of an embodiment of the immobilization device.
Figure 6:
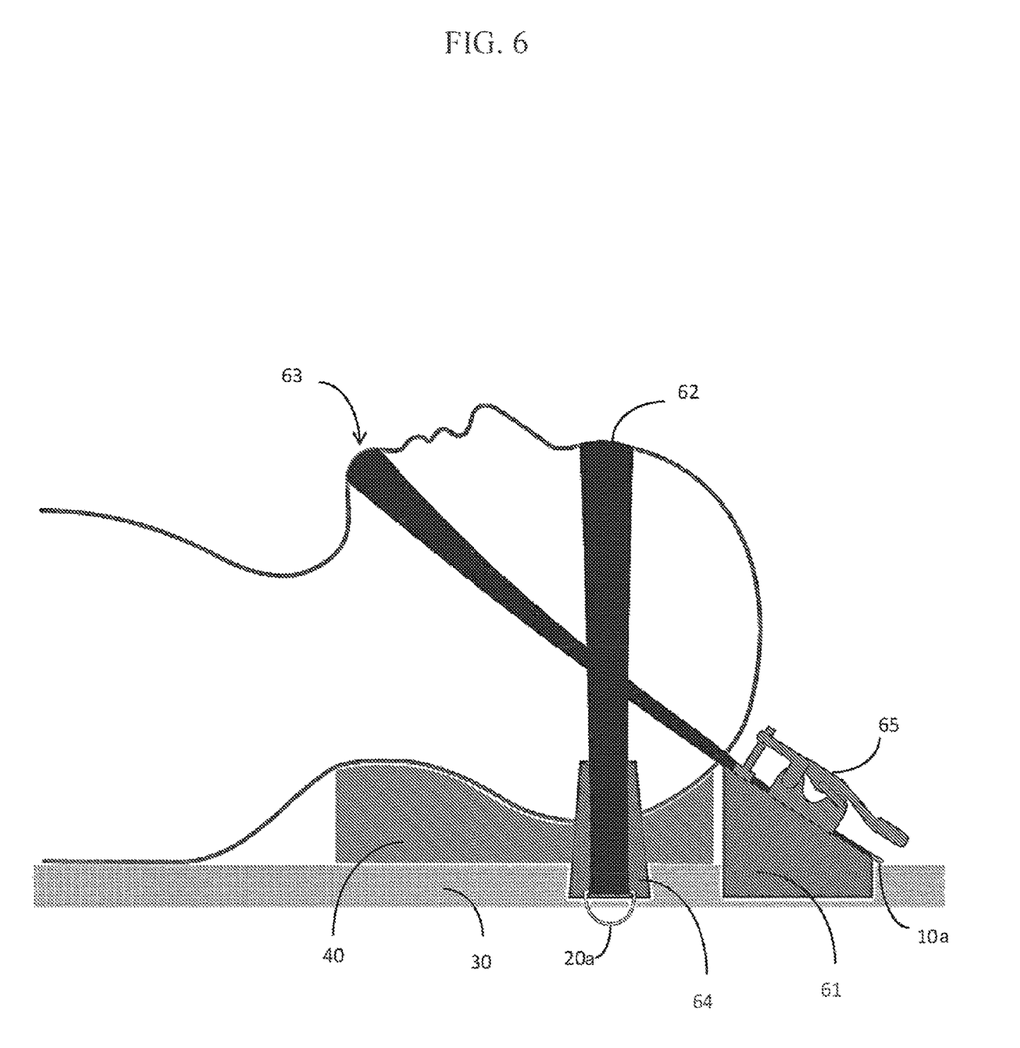
FIG. 6 depicts a further embodiment of the immobilization device further using a clamp and a force gauge.

FIG. 4 further depicts that the straps 2 and 3 connect to both sides of the patient. As can be seen a second attachment means 25 is placed on the opposite side of the force gauge 20 and a second attachment means 15 applied on the opposite side of the force gauge 10. Accordingly, this allows the straps to be securely connected to each side of the surface 30. The clamps 65, depicted in FIG. 4, and further defined in FIGS. 6 and 9, are used to secure the straps in place, especially when the strap needs to have a precise force applied to said strap. The clamp here, allows the strap to extend through the clamp, a force gauge attached at the end of the strap, and then to clamp the strap tight. For example, hand pressure can pull on the force gauge, in turn, pulling on the strap, until a predetermined force is reached. At that point, the clamp can be secured, and the force gauge removed, as the strap is secured at the determined force.

Figure 5:
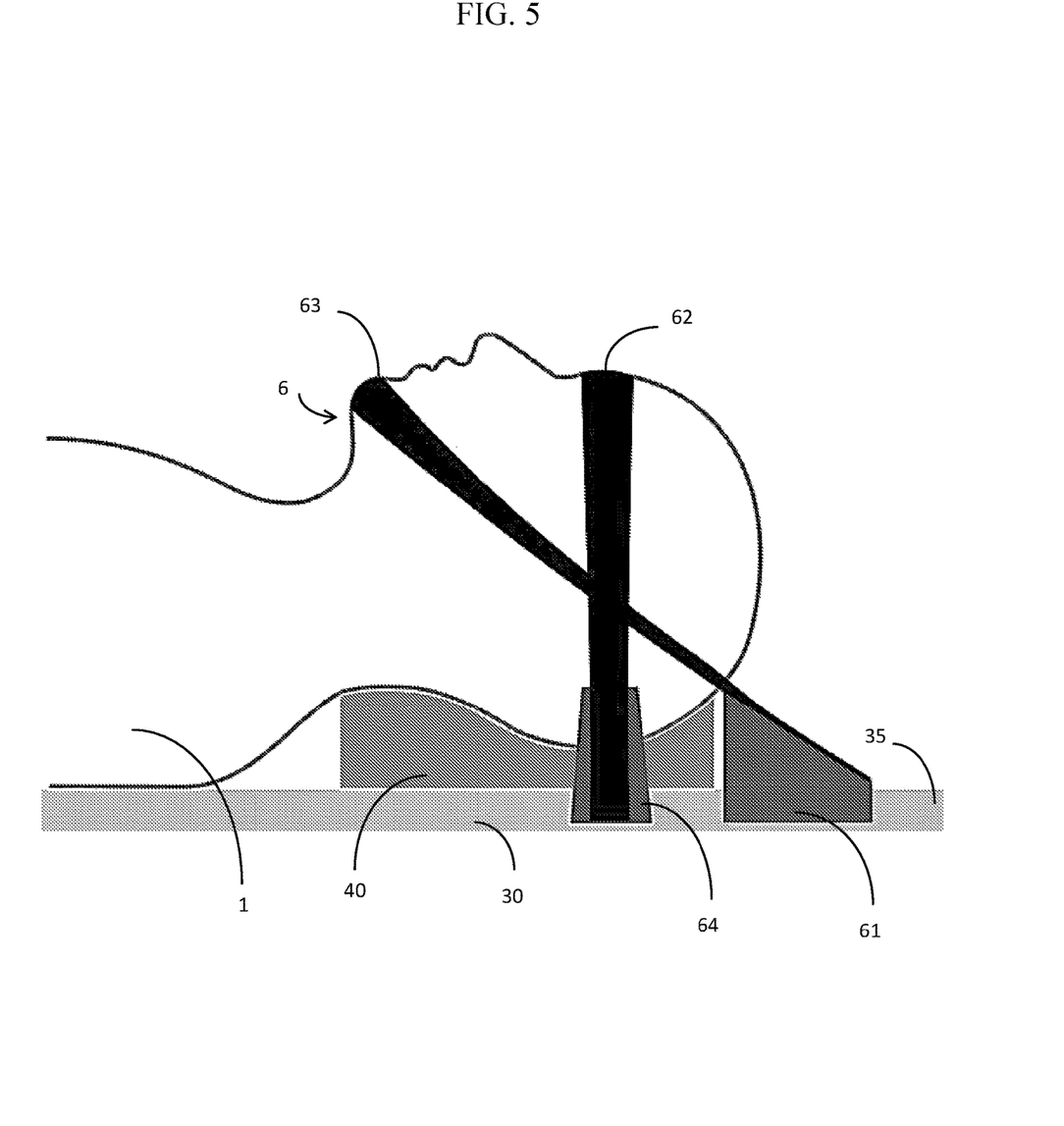
FIG. 5 depicts a variation of the immobilization device.

FIG. 5 further depicts a modified embodiment, wherein a patient is laying supine on a surface 30, with the patient's head and neck positioned in a cradle 40. A first strap 62 is connected at one side of the surface 30, with an approximate position in line with the forehead of the patient. As provided in the prior figures, the first strap 62 can be positioned along the linear side of the surface 30 with a first anchor 64, and then allow for the first strap 62 to cross across the face of the surface 30 over the patient's forehead and connect on the other side of the surface 30. By positioning the first strap 62 properly, the strap is nearly parallel to the top 35 of the surface.

A second strap 63 is defined with an anchor 61 that is positioned between the first strap anchor 64 and the top 35 of the surface. The second strap 63 crosses over or under the first strap 62, towards the chin 6 of the patient, and then crosses back over or under the first strap 62 to connect to a second anchor on the opposing side of the surface 30. Anchors are provided on each side of the surface 30, the right side being a mirror image of the left side with respect to the positioning of the anchors 61 and 64.

FIG. 6 depicts a further clamp 65 that can be attached to the second strap anchor 61. This clamp 65 can be used to secure the second strap 63 in place. For example, a force gauge 10 attaches to the second strap 63 by using, e.g., a D-ring 10a at the opposing end of the strap, wherein the D-ring 10a engages to the force gauge 10, in the manner shown in FIG. 7, and the strap is tightened by pulling hooking the force gauge to the strap and puffing the force gauge until a predetermined force is reached, wherein the clamp 65 is applied, locking the strap into place with that predetermined amount of force being applied and maintained on the second strap 63. This gives a highly reproducible amount of force to the second strap 63 and to the patient 1, allowing for reproducible and secure immobilization. A clamp is only needed on one side of the surface. The strap is secured on one side of the surface, with the other end of the strap free. The patient is positioned on the face of the surface and the straps pulled over the patient. Threading the strap through the clamp, and applying a force gauge to the free end of the strap, then allows a user to pull on the force gauge to meet a predetermined force, or if applying for the first time, a comfortable, but secure force. Once that force is met, the clamp is activated, and compressed down to secure the free end of the strap into place.

Figure 7:
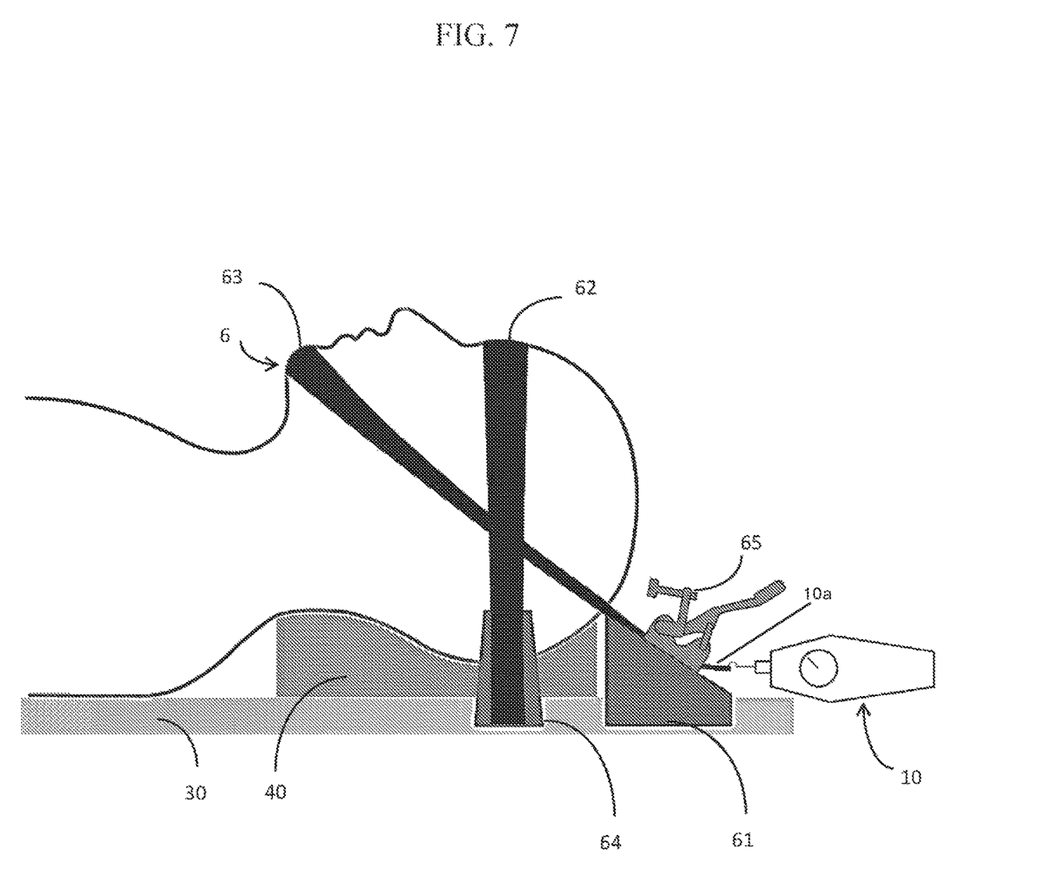
FIG. 7 depicts a further embodiment of the immobilization device using a clamp and force gauge.

A second force gauge 20 (not shown in this figure) is connected to the first strap 62 by using, e.g., a D-ring 20a at the opposing end of the strap 62, wherein the D-ring 20a engages to the force gauge 20, in the manner shown in FIG. 7 with regard to the D-ring 10a and force gauge 10. This force gauge 20 confirms a consistent and comfortable pressure to be applied to the forehead of the patient during the procedures. However, the precise force is not critical, as this does not impact the degree of neck extension of the patient. Accordingly, in this embodiment, the force gauge 20 is optional, as it is not implicated on the control and degree of patient neck extension.

FIG. 7 depicts the second strap anchor 65 in an open position. Accordingly, in such open position, a user would impart a force onto the second strap 63, and pull on the force gauge 10 to reach a predetermined force. After reaching said force, the clamp 65 can be moved from the open position, as depicted in FIG. 7 to the closed position as depicted in FIG. 6, in order to lock the second strap 63 with that precise force. This ensures that there is a reproducible amount of force applied to the patient's chin with a particular neck extension.

Figure 8:
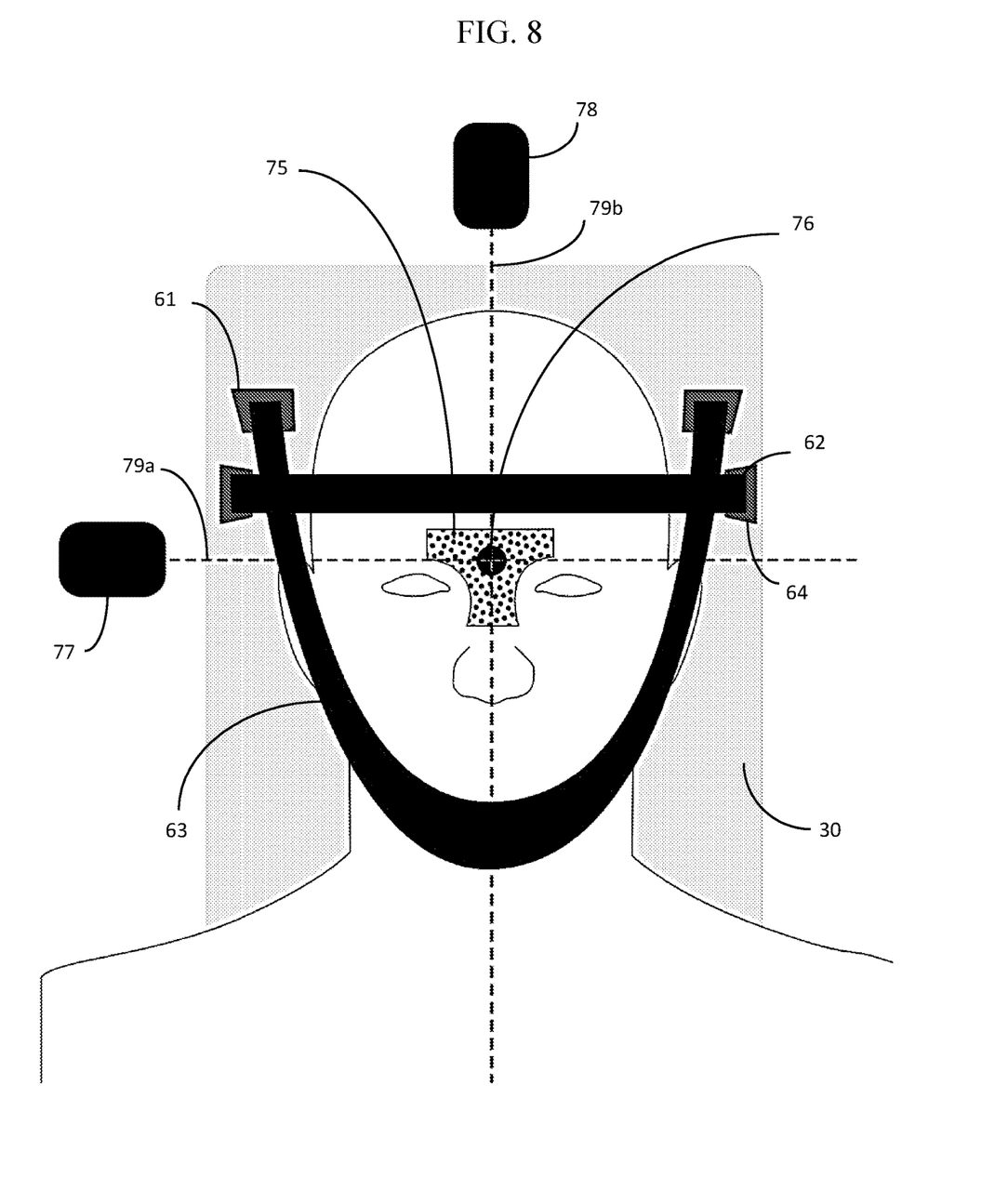
FIG. 8 depicts a top plan view of a patient being immobilized with the immobilization device, and further comprising a nose bridge and laser setup components.

FIG. 8 further depicts the relative position of the first 62 and second straps 63 as the first strap 62 crosses over the forehead and the second strap 63 crosses beneath the chin 6. Placed on the face of the patient, at the bridge of the patient's nose, is a nose bridge 75. The nose bridge 75 is preferably a small piece of thermoplastic mesh material that is warmed in a water bath (standard for this material) for malleability and then placed on the bridge of a patient's nose and upper orbit, to mold according to the patient's bony anatomy. This nose bridge 75 is then provided with a marker 76 comprising two perpendicular lines as depicted in FIG. 8. These perpendicular lines are aligned to a laser setup lights, for example lasers 77 and 78, which emit a laser 79a and 79b, can be visually aligned along the marker 76 on the nose bridge 75. This ensures that the patient's positioning is identical each day, by confirming both the force on the force gauge 10 and or 20, as well as positioning the marker 76 and the laser lines 79a and 79b along the marker 76. The setup straps are then tightened by applying the appropriate force. The patient position is confirmed by verifying that the crosshair on the nose piece are still in line with the laser light intersection and consistent force is applied to each strap. This immobilizes the patient in a defined position suitable for repeated positioning.

The apparatus can therefore be utilized to immobilize a patient to a surface 30 and to provide for replicable placement of the patient for certain medical treatments such as radiation therapy. Accordingly, certain methods of treatment and methods of securing a patient are possible with such an apparatus.

For example, a method of reproducibly immobilizing a patient on a radiation surface comprises: positioning a patient on a surface with said patient's head in a cradle; attaching a first strap across the forehead of the patient, with the strap anchored approximately perpendicular to the longitudinal axis of the surface, and each anchor being approximately in line with the first strap; attaching a second strap around the chin of the patient, wherein the second strap is anchored on each side of the surface between the top of the surface and the first strap anchors, thus crossing the first and second straps over one another on each side of the head of the patient; determining a force for the second strap to define neck extension; engaging a nose bridge to the patient, said nose bridge conformed to uniquely fit the patient, said nose bridge comprising a marker having two perpendicular lines on said marker; engaging said marker with at least one laser to align said laser with at least one line of the marker. Preferably, the specific position and relative position of the components is memorialized, wherein said same positions can then be reproduced on a subsequent time.

It is further considered that in some embodiments, the straps 2, 3, and 4, have a small amount of elasticity to allow them to be secured around the patient, but to give, slightly, and therefore allow a predetermined length strap to be modified by the amount of force applied to the force gauges. By having some elasticity in the strap, the force can be applied but have a small amount of give or movement to the strap and to the patient, but maintain the next extension position and nose bridge position to ensure reproducible positioning of the patient.

In further embodiments, the straps are intended to have very little elasticity, and the force and the length of the straps in such cases are appropriately amended by a ratcheting mechanism or other mechanism to modify the length of the straps being utilized in securing the patient.

In view of the apparatus, certain methods of using the apparatus for securing a patient, or for administering treatment are particularly relevant. A first method comprises the steps of placing a patient on the surface 30 so that the patient's head is resting on the head/neck cup or cradle 40, and the cradle 40 then rests on the surface 30. Further the cradle 40 can be secured into place on the table 30 and the positon accurately marked and determined based on notches or markings on the table 30. A chest strap 4 is secured around the patient. A chin strap 3 is secured around the chin of the patient and tightened slightly. A forehead strap 2 is secured around the patient's forehead and tightened. The chest is secured tightly to the patient. The chin strap is tightened to a predetermined force as measured on a first force gauge. The forehead strap is further tightened to a predetermined force as measured of a second force gauge. The patient is thereby in position for receiving treatment to the head or neck. The patient's position is replicable by determining the force applied on each strap to each of the two force gauges through attaching a force gauge to one end of each strap, with the opposing end attached to the surface. By pulling on the force gauge, a precise force can be applied to each strap, and the strap secured into place with said force, to define the replicable position.

In a further embodiment the above method includes a further step of determining the length of the strap and then applying the appropriate force to said strap on said patient.

In a further embodiment, the patient is first secured to a surface 30 and the appropriate length of each strap is determined and the force for each strap is determined. The position of each strap is identified with regard to notches on the surface 30 and the position of the head against the cradle 40. The patient is administered treatment and the straps are relieved. Upon a subsequent administration of treatment, the patient is placed on the surface 30, and the length of each strap, the force of the strap and the positon of the straps based on the notches are confirmed. By meeting such criteria, the position of the head and neck of the patient is replicated to allow for subsequent treatment to the patient.

Patients are setup on the radiation treatment table with the device platform underneath them. The patient's head is placed in a standard headrest cup/cradle as shown in FIG. 5-7). The chin strap e.g. the second strap 63, is then placed under the patient's chin 6 and the appropriate force needed for comfortable immobilization is applied by pulling on the strap with the mobile force gauge. When the proper force is applied, the toggle clamp 65 is locked into place, applying a perpendicular force against the strap and maintaining the force on the patient's chin 6. The force gauge 10 can be removed from the first strap (or a second force gauge independently used) and is then used to apply a similar force to the forehead strap (first strap 62) and the second toggle clamp locked in place. The force gauge is then removed from the setup.

In a setup where the force gauges are integrated into the treatment platform (such as FIG. 2) the force on the strap can be applied by a ratcheting mechanism that shortens the strap length or pulling on the strap by hand while viewing the force gauge reading.

After a patient is immobilized, a thermoplastic nose piece/nose bridge 75 is then molded to the patient's nose bridge and orbital bone (applied as soft/malleable only at the initial time of simulation; all subsequent times it will be placed as a hard contour piece to the same place on the patient's nose) and the cross hair/marker 76 on the nose piece aligned to the laser setup lights e.g. lasers 77 and 78, as one embodiment of laser lights, indicating the reproducible patient position. The patient's bilateral canthuses are also used to help determine the proper tilt of the patient's head. The Cartesian coordinate positions of the cross hairs of the marker 76 and canthuses in reference to the table position (height and horizontal displacement) are recorded and reproduced with each treatments. Optionally, a cone beam computer tomography scan is then acquired to verify patient position and any needed translational shifts made as per standard treatment procedure.

Examples of the mask in therapeutic use include immobilization for head and neck cancers, brain cancers and skin cancers of the head and neck or extremity.

We tested an embodiment of the invention as compared to a typical thermoplastic mask. For purposes here, the thermoplastic mask is defined as thermoplastic mesh material that is molded to the anatomy of the patient in position for radiation treatment for the purpose of patient immobilization, such as those defined in the prior art referenced in the background. We then compared the translation shifts between the thermoplastic mask and our device to determine whether they were similarly reproducible.

Our data indicates that the patient's bony anatomy, as determined by cone beam computer tomography at the time of radiation treatment, has similar degrees of translational error using the thermoplastic mask of the prior art as with the strap and force gauge immobilization described herein. Therefore, our system provides for a replicable immobilization device in line with the currently available systems. However, the largest hurdle for use of thermoplastic masks remains the anxiety generated from use of the device.

In order to evaluate anxiety between the two devices, we compared anxiety scores for patients using the thermoplastic mask and the invention as described herein. Our anxiety score data indicate that patients find the strap immobilization to be more tolerable than the thermoplastic mask. Indeed, patients prefer the strap immobilization compared to the thermoplastic mask, noting that it is less anxiety provoking.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A replicable immobilization device comprising:
A surface, first and second straps, and a force gauge; wherein the surface is substantially flat having a surface face, a length and width sufficient to support a human patient, a top and, two sides; the first strap is attached on one end to one side of the surface, an opposing end being free; wherein the free end, crosses over the surface face and engages a connecting means on the opposing side of the surface; the second strap having one end secured on one side of the surface and an opposing end of the second strap being free; said free end of the second strap engaging to the connecting means on the opposing side of the surface, and engaging with a force gauge on the opposing side; wherein the force gauge quantifies a force applied to the second strap; wherein the quantified force can be replicated for subsequent immobilization,
further comprising a nose bridge and a laser, said nose bridge comprising a marker for engaging to said laser for orienting the nose bridge to a specific location based on the laser position.

2. The device of claim 1, further comprising a second force gauge.

3. The device of claim 1, wherein the free end of each strap comprises an attachment means to secure to the force gauge.

4. The device of claim 1, wherein the connecting means is defined as a first and a second strap anchor positioned on one side of the surface for connecting the free end of the first and the second straps.

5. The device of claim 4, wherein each of the first and the second strap anchors comprise a clamp for securing a strap to the strap anchor.

6. The device of claim 1, wherein each strap comprises a D-ring at the opposing end of the strap, wherein the D-ring engages to a force gauge.

7. A method of immobilizing a patient for radiation therapy comprising:
   securing a first strap to a radiation therapy table, one end of said strap engaged to one side of the radiation therapy table, and an opposing end crossing over said radiation therapy table and securing to a strap anchor on the opposing side of the radiation therapy table;
   securing a second strap to said radiation therapy table, one end of said second strap connected to one side of the radiation therapy table and an opposing end of the second strap connected to a force gauge; wherein said second strap engages with said patient to define a degree of neck extension;
   administering radiation therapy to said patient,
   the method further comprising:
   placing a nose bridge between the first and second straps, wherein said nose bridge is engaged to said patient, and wherein said nose bridge comprises a marker; and
   detecting said marker with a laser.

8. The method of claim 7, comprising securing a third strap to said radiation therapy table.

9. The method of claim 7, further comprising determining a force from the force gauge and determining a degree of neck extension.

10. The method of claim 7, further comprising determining a force from the force gauge and determining a degree of neck extension; wherein said force and degree of neck extension can be replicated for re-positioning of the patient for a subsequent round of radiation therapy.

11. A replicable immobilization device comprising: a surface, a first strap and a second strap, and two force gauges; wherein the surface is substantially flat and has a length and width sufficient to support a human patient, a top edge and two side edges; the first strap having a first end connected to one side edge, and an opposing end connected to the opposing side edge, wherein a portion of the first strap contacts a portion of a body being immobilized; the second strap having a first end connected to one side edge, and disposed between the first strap and the top edge, and an opposing end connected to the opposing side edge, also between the top edge and the first strap, wherein a portion of the second strap comprises a concave recess for securing around the portion of the body being immobilized; each of the first and the second straps comprises a force gauge positioned on the first and second straps, wherein the force gauges provide a reading of the force applied to each strap,
   further comprising a nose bridge having a marker that comprises a pair of intersecting lines; and wherein said device further comprises at least one laser, said at least one laser oriented to intersect with at least one of the intersecting lines of said nose bridge to define a position of said nose bridge.

12. The immobilization device of claim 11, further comprising a neck cradle positioned on the surface.

13. The immobilization device of claim 11, wherein said nose bridge is formed from a thermoplastic material, and said marker is arranged on a top surface of said nose bridge.

14. The immobilization device of claim 11, wherein each force gauge is parallel to the direction respective of one of the first and second straps on which it is positioned.

15. The immobilization device of claim 11, further comprising a first and a second strap anchor positioned on the opposing side edge of the surface, and a clamp positioned on each first and second strap anchor.

16. The immobilization device of claim 15, wherein each said clamp receives the opposing end of the respective strap, having the anchor on which it is positioned, and wherein each said clamp operates between an open and a closed position, suitable to secure the respective strap to said respective strap anchor.

17. The immobilization device of claim 11, wherein after immobilization, the human patient receives radiation therapy.

18. A replicable immobilization device comprising: a surface, a first strap and a second strap, and two force gauges; wherein the surface is substantially flat and has a length and width sufficient to support a human patient, a top edge and two side edges; the first strap having a first end connected to one side edge, and an opposing end connected to the opposing side edge, wherein a portion of the first strap contacts a portion of a body being immobilized; the second strap having a first end connected to one side edge, and disposed between the first strap and the top edge, and an opposing end connected to the opposing side edge, also between the top edge and the first strap, wherein a portion of the second strap comprises a concave recess for securing around the portion of the body being immobilized; each of the first and the second straps comprises a force gauge positioned on the first and second straps, wherein the force gauges provide a reading of the force applied to each strap,
   wherein each strap defines a strap orientation angle, as compared to the flat surface, wherein the strap orientation angle and the force define a specific immobilization parameter.

* * * * *